United States Patent [19]

Jibelian

[11] 4,226,112
[45] Oct. 7, 1980

[54] METHOD AND APPARATUS FOR ANALYZING GASES

[76] Inventor: Gomidas Jibelian, 740 Fawn Dr., San Anselmo, Calif. 94960

[21] Appl. No.: 873,617

[22] Filed: Jan. 30, 1978

[51] Int. Cl.³ ............................................. G01N 31/08
[52] U.S. Cl. ..................................................... 73/23.1
[58] Field of Search .................. 73/23.1, 23; 128/2 C, 128/2.07, 718, 719, 724; 422/89; 23/232 C

[56] References Cited

U.S. PATENT DOCUMENTS

| | | | |
|---|---|---|---|
| 3,056,277 | 10/1962 | Brenner | 73/23.1 |
| 3,134,257 | 5/1964 | Reinecke | 73/23.1 |
| 3,330,150 | 7/1967 | Loyd et al. | 73/23.1 |
| 3,895,630 | 7/1975 | Bachman | 73/23 |
| 3,927,670 | 12/1975 | Turney et al. | 73/23.1 |

*Primary Examiner*—Stephen A. Kreitman
*Attorney, Agent, or Firm*—Edward B. Gregg

[57] ABSTRACT

Apparatus and method for analyzing gases, especially respiratory gases for oxygen and carbon dioxide content, and for measuring pulmonary functions; such comprising a detector employing thermistors forming parts of a Wheatstone bridge circuit, one of which is in contact with a carrier gas, the other with a sample of the gas to be analyzed sandwiched between carrier gas in advance of and trailing the sample, the output of the detector being sensed by a recorder and transduced into a tracing; the gas to be analyzed being passed through a column or columns of adsorbent material which selectively retains certain components of the gas and releases them in a time ordered sequence; the test thermistor having its temperature varied in accordance with the composition of the gas; the adsorptive material being selected as to its composition and geometry to bring about separation and release of components of the gas in a time ordered sequence and within a very short period of time; the gas circuit being adapted to minimize errors in the voltage peaks corresponding to components of the gas.

6 Claims, 5 Drawing Figures

METHOD AND APPARATUS FOR ANALYZING GASES

This invention relates to an apparatus and to a method for gas analysis by chromatographic technique employing a detector, which typically is a Wheatstone bridge circuit having thermistor elements which respond to the thermal conductivity of a gas and produce a signal, the magnitude of which is a measure of the thermal conductivity of the gas, hence of its composition.

More particularly this invention relates to a chromatograph-thermal conductivity apparatus and method for analyzing expired gas from human lungs (i.e., for measurements of the $CO_2$ and $O_2$ concentrations in expired air), and to determine pulmonary function (i.e., the rate at which inhaled air is utilized by the lungs and the efficiency of transfer of oxygen from inhaled air to the bloodstream and of carbon dioxide from the bloodstream to the exhaled air). The invention is also useful for determining pulmonary blood circulation and for gas analysis in general.

A well-known technique for the analysis of expired air and for measuring pulmonary function employs a solid-gas phase adsorber and a detector which measures the thermal conductivity of the gas and provides a signal which can be read out on a recorder to display peaks which are a measure of the concentrations of the components of the gas. The basic principles of this technique, which are elaborated in the literature, for example, in Keulmans, Gas Chromatography, Reinhold, New York, 1957 and Hamilton, Smith and Cory, American Journal of Medical Electronics, 1964, vol. 3, pages 3-15, are as follows:

If the apparatus employs thermistors, a pair of thermistors is used as elements of a Wheatstone bridge circuit. A thermistor includes a ceramic semi-conductor which is heated by the current passing through it and it is cooled by a current of gas flowing over it. A carrier gas is caused to flow over one such ceramic semiconductor and the gas to be analyzed is propelled over the other ceramic semi-conductor by the carrier gas. The different gases (carrier gas and gas to be analyzed) have different thermal conductivities and therefore cool the heated thermistors by different amounts, the difference resulting in an output from the bridge which is recorded on a recorder instrument. By means of reference gases of different but known compositions the apparatus may be calibrated whereby the peaks on the recorder readout measure the composition of the gas to be analyzed.

Instead of thermistors, katharometers may be used but for present purposes thermistors having very small and therefore very sensitive ceramic semiconductors are preferred. The size of the ceramic semiconductors is selected to have a very fast response to fluctuations of gas composition.

In such an apparatus there is provided one or more solid phase adsorbers through which the gas to be analyzed is passed. The effluent gas from the adsorber is passed over the test thermistor of the detector and a carrier gas is passed over the reference thermistor. The solid adsorbent employed in the chromatograph is selected to that it will absorb one or more components of the incoming gas, will hold one or more of the adsorbed components for a period of time, and will then release the adsorbed component or components over a period of time. (The terms "adsorber", "adsorption" and "adsorbent" include molecular sieves and materials which function more like ion exchangers.)

For the sake of illustration, suppose that a three component gas is to be analyzed, comprising a carrier gas such as helium (He) and two other molecular species ($G_1$ and $G_2$), and suppose that the material in the adsorption column has no affinity for He but has a greater affinity for $G_1$ and a lesser affinity for $G_2$. Suppose further that the reference thermistor and the test thermistor are exposed to a stream of He and that a sample of the gas to be analyzed ($G_1$ and $G_2$) is then propelled through the adsorption material, then over the test thermistor, followed by pure He. The first increment of the gas flowing through the adsorption material will be He, therefore the two thermistors, being exposed to the same gas (He) will be at the same temperature and the detector will have no output. This condition will be recorded on the tracing of a recorder as the base line. Then $G_2$ will be eluted and the concentration of the effluent gas (He+$G_2$) will have an increasing, then a decreasing, proportion of $G_2$. This will result in a peak on the recorder tracing corresponding to the rise and fall of the $G_2$ concentration in the effluent gas from the chromatograph. Thereafter, $G_1$ will be eluted, its concentration in the effluent gas (He+$G_1$) will rise and then fall and the tracing will show a corresponding peak.

By the use of reference gases of known composition (He+$G_1$+$G_2$ in different proportions) the apparatus can be calibrated so that the peaks ($G_2$ peak and $G_1$ peak) will be a measure of the concentrations of $G_2$ and $G_1$ respectively in the gas to be analyzed.

This technique offers advantages over other techniques such as chemical analysis and infra-red absorption. One of its advantages is its relatively low cost. However, it will be apparent that the seeming simplicity of this apparatus rests upon certain assumptions. One of these assumptions is that the peaks will be distinct and sharply separated and that the tracing of each peak will start from the same base line or close to it, will rise sharply from the base line, and will return sharply to the same base line or close to it. If these conditions are not fulfilled, e.g., if there is overlap of tracings of the peaks or tailing (a gradual rise or fall of a peak from or to the base line), errors will result.

Heretofore some commercially available apparatus of this type require the use of heat to heat both the reference katharometer and the test katharometer. It is an advantage to be able to work at ambient temperature, but such commercially available apparatus is not suitable for use in ambient temperature.

Among other disadvantages of presently available apparatus of this type are expense of the apparatus, inability to analyze for certain gases, for example, high oxygen concentration because the latter burns or oxidizes the katharometer filament operating at a high temperature; the need for switching during a single analytical procedure to measure first one molecular species and then another. It is not intended to imply that all presently available apparatus of this character suffers from all of these disadvantages, but insofar as I know, they all suffer from one or more such disadvantages.

It is an object of the present invention to provide apparatus and a method of the general character described which offers one or more of the following advantages:

(1) The apparatus may be employed at room temperature, that is to say, it does not require an oven or a heating element.

(2) Analysis can be carried out in not more than about one minute.

(3) A small (for example, 3 milliliter) sample of the gas to be analyzed is sufficient.

(4) No switching is required during the course of a single analytical procedure.

(5) Small proportions of a molecular species may be analyzed with a high degree of accuracy.

(6) The apparatus will analyze for oxygen, carbon dioxide, carbon monoxide, acetylene, neon and helium.

(7) No experienced personnel required to use it and maintain it.

The above and other objects of the invention will be apparent from the ensuing description and the appended claims.

One embodiment of the invention is illustrated by way of an example in the accompanying drawings in which FIG. 1 is a schematic illustration of the apparatus of the invention.

Figure 1:
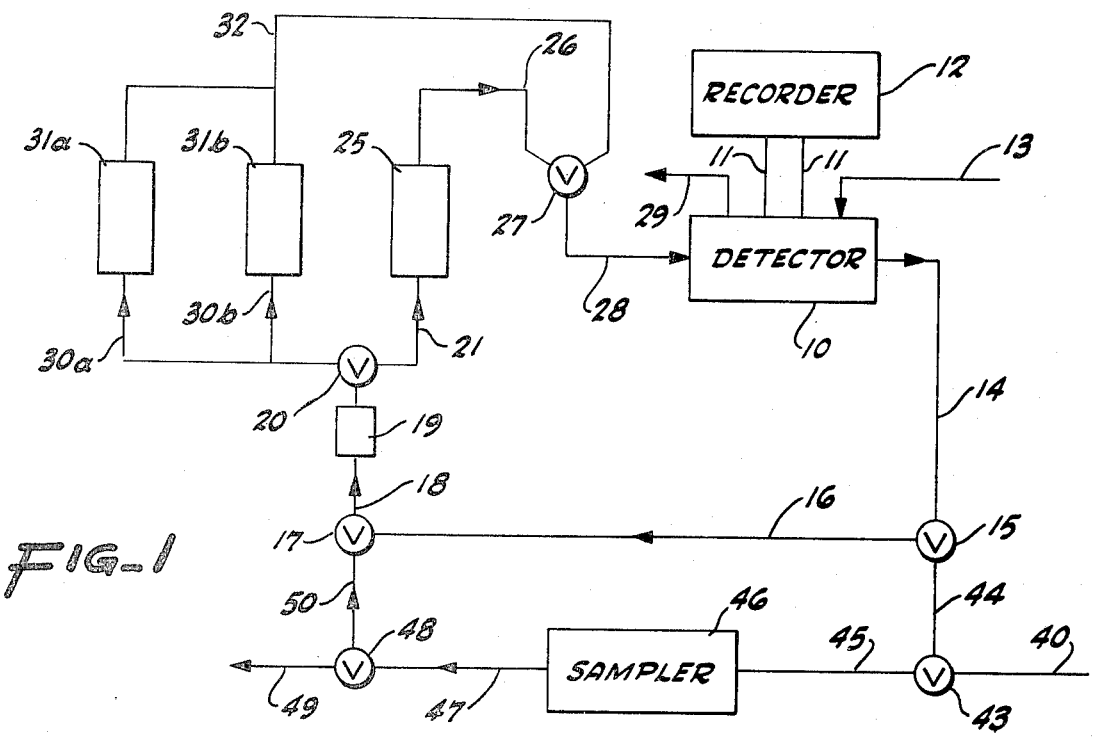
Figure 2:
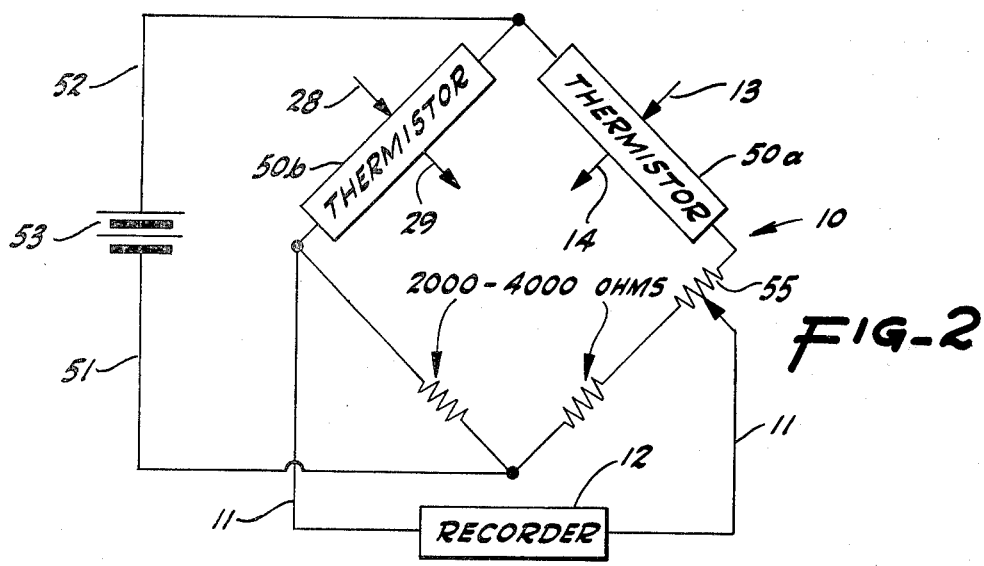
FIG. 2 is a schematic illustration of the detector circuit.

Referring now to FIG. 1, a detector 10 is there shown and is shown in more detail in FIG. 2. It is shown as being connected by wires 11 to a recorder 12. The recorder 12 may be of a known type, for example, a Honeywell strip chart recorder, a Varian aerograph, etc., which records the output of the detector 10 continuously on paper. As is well known in the art, the detector 10 or the recorder 12 may embody (and usually will embody) an adjustable attenuator (not shown) to attenuate the output of the detector so that the tracings of interest do not go off scale.

A conduit 13 is provided which is connected to a tank (not shown) of carrier gas, for example, helium. The supply is regulated manually or automatically by a suitable valve (not shown). The carrier gas is usually a single molecular species and is inert, e.g., helium or argon. It serves to bathe the reference thermistor and to propel a sample of the gas to be analyzed through the adsorption material and the detector.

The carrier gas flows through the detector 10 in contact with the reference thermistor shown and described below in connection with FIG. 2, thence through a conduit 14 to a valve 15. The valve 15 is one of several valves (the valves 15, 17, 27, 43 and 48) which are of known construction and may be of various types, e.g., piston valves, rotary valves, etc., and may be variously operated. However, the valves 15, 43, 48 and 18 are preferably solenoid valves such as manufactured by Linear Dynamics Company of Millis, Massachusetts. Such valves employ the rod of the solenoid as the operating valve member (as a piston) to open and close the ports of the valve rather than as a valve operator to operate a separate valve. I have found that the use of such solenoid valves accelerates valving and contributes to speed and accuracy of analysis.

In its normal or de-energized condition valve 15 routes gas through shunt line 16 to a valve 17 which is normally in a position to route gas from line 16 through line 18 and drying tube 19 to valve 20. (Drying tube 19 may contain, for example, calcium chloride.) Valve 20 can be set in either of two positions, one of which routes gas through line 21 to adsorption column 25, thence through line 26 and valve 27, to line 28 leading to detector 10 wherein this gas contacts a thermistor (the test thermistor) shown and described below in connection with FIG. 2. The gas leaves the system through line 29.

The other setting of valve 20 causes the gas to flow in parallel through lines 30A and 30B to adsorption columns 31A and 31B respectively, then through line 32, valve 27, line 28 and detector 10. For the particular purpose described in Example 1 below, columns 31a and 31b are designed so that the gas flow through columns 31A and 31B are in the desired proportions.

The valves 20 and 27 are interlocked such that when valve 20 is set to route gas through columns 31A and 31B, valve 27 communicates with line 32 and when valve 20 is set to route gas through column 25, valve 27 communicates with line 26.

The gas to be analyzed, taken from a suitable source, enters the system through line 40. Thus gas expired by a patient is collected in a balloon (not shown) and is introduced into line 40 or a mouthpiece (not shown) is directly connected to line 40 so that the patient's breath may be taken directly. This sample of gas then passes through valve 43 and line 45 to a sampler 46. Typically sampler 46 has a volume of 3 milliliters. The outlet of sampler 46 is shown as a conduit 47 connected to a valve 48 which in its normal, de-energized condition vents to atmosphere through line 49. The other port of valve 48 is connected by a line 50 to valve 17.

Referring now to FIG. 2, a Wheatstone bridge is shown including in one of its legs or branches a reference thermistor 50A and in another branch a test thermistor 50B. The gas lines 13 and 14 which bathe reference thermistor 50A in reference gas are shown as are the lines 28 and 29 which bathe the test thermistor 50B in the gas to be analyzed. The recorder 12 is shown connected to the Wheatstone bridge by wires 11. Also shown are wires 51 and 52 and power source 53. Thermistors 50A and 50B are preferably selected, each to have a resistance of 5000 to 7000 Ohms at room temperature and to have a resistance of 500 Ohms at room temperature when carrying a current of 6 milliamps. Identical 2000 to 4000 Ohm resistors are incorporated in the other branches of the circuit as shown. Also shown is a potentiometer 55 (typically a 200 Ohm, 10 turn potentiometer to balance the bridge).

Figure 3:
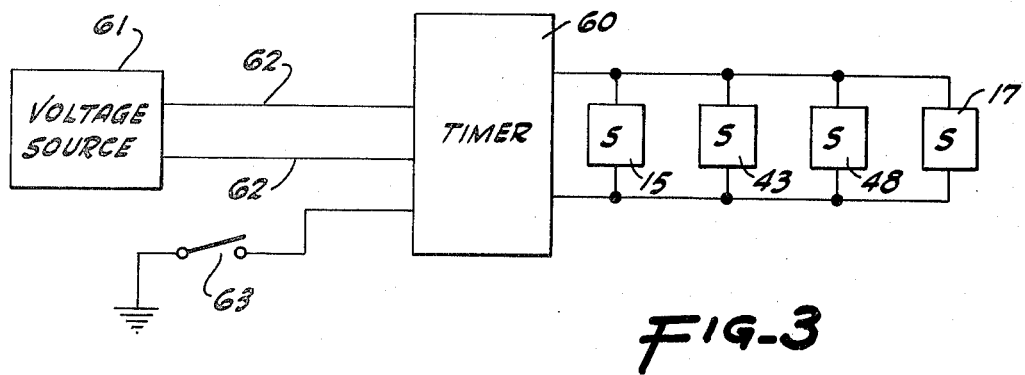
FIG. 3 is a schematic view of a circuit for controlling timing of operation of the valves shown in FIG. 1.

Referring now to FIG. 3, a timer 60, voltage source 61 and connections 62 are shown together with analysis switch 63 and solenoid valves 15, 43, 48 and 17 which, as will be seen, are connected in parallel whereby when analysis switch 63 is open these valves are in the "shunt" (de-energized) position described above. That is, carrier gas passes through shunt line 16. Meanwhile valve 43 is open to lines 40 and 45 and valve 48 is open to lines 47 and 49. In this mode carrier gas passes in through line 13, through shunt line 16, through column 25 or columns 31A and 31B according to the setting of valve 20, then out through line 29. Meanwhile sampler 46 is filled with gas to be analyzed. When analysis switch 63 is closed, timer 60 starts, solenoid valves 15, 43, 48 and 17 are energized and gas flow is through lines 14, 44, 45, sampler 46, line 47, line 50, line 18, etc. Timer 60 (which may be any of several known, commercially available timers) is set to restore valves 15, 43, 48 and 17 to their original, de-energized positions and to open analysis switch 63 after a short interval of time, typically 5 seconds after the sample of bolus of gas in sampler 46 has passed through valve 17 but before adsorbed gaseous components are eluted by carrier gas from column 25 or columns 31A and 31B. The volumes of sampler 46 and dryer 19 are large compared to the volume of the lines. The volume of dryer 19 can be tolerated but if carrier gas continues to flow through sampler 46 a phenomenon known as longitudinal diffusion occurs which results in altering the shape of the peaks.

In operation the apparatus functions as follows: Carrier gas is introduced through line 13 and is caused to flow through lines 14, 16, 18 and either column 25 or columns 31A and 31B according to the setting of valve 20. Meanwhile the gas to be analyzed enters through line 40, valve 43 and line 45 into sampler 46, the outlet of which is connected to atmosphere by line 47, valve 48 and line 49. The sample is introduced either indirectly from a patient by exhaling into a balloon or directly by a patient exhaling into a mouthpiece. An excess is introduced so that the sampler 46 is entirely filled with this gas at atmospheric pressure, the excess being vented to the atmosphere. As a result, a predetermined sample or bolus of gas is collected at atmospheric pressure and it also assumes ambient temperature.

The analysis switch is then closed. This resets valves 15, 43, 48 and 17 and starts timer 60 and causes carrier gas to flow through line 14, valve 15, line 44, valve 43 and line 45 to sampler 46. This acts as a piston to drive the sample or bolus of gas in sampler 46 through line 47, valve 48, line 50, valve 17, line 18, drying tube 19 and valve 20 to column 25 or to columns 31A and 31B according to the setting of valve 20, then through line 26 (or line 32), valve 27 and line 28 to detector 10, then over thermistor 50B and out through line 29.

The timer resets the valves 15, 43, 48 and 17 to their original positions after the lapse of a predetermined time, usually about 5 seconds, to cause resumption of flow of carrier gas through shunt line 16 and then through column 25A or columns 31A and 31B, etc.

The following examples of analysis of respiratory gases (Example 1) and analysis of gases to determine pulmonary function (Example 2) will further illustrate the practice and advantages of the invention.

EXAMPLE 1. ANALYSIS OF RESPIRATORY GASES

For the purpose of measuring the $CO_2$ and $O_2$ content of respiratory gas, a sample of such gas is introduced as described into sampler 46. The valve 20 is set so that it will connect the gas flow to parallel columns 31A and 31B. The lengths of columns 31A and 31B are such that two volumes flow through column 31B for each volume flowing through column 31A. Column 31A contains a molecular sieve, preferably one that is known as 13X. This is diatomaceous earth. For this purpose a column of 13X is employed which is $\frac{1}{4}''$ in diameter and 44 inches $\pm 2$ inches in length, such dimensions having been found to be advantageous. This column (likewise column 31B) may be coiled to provide the desired length in a more compact form. Column 31B preferably contains an adsorbent such as Porapak Q which is a product of Waters Associates of Milford, Massachusetts. This is described in literature of that company as being in the form of beads of very rigid cross-linked polymers having a surface area of 500-600 sq.m. per gram and a density of 0.34 gram per cubic centimeter. It is a polystyrene. Column 31B is preferably $\frac{1}{4}$ inch in diameter and 14 inches $\pm 1$ inch in length. These materials are conditioned as follows: 13X is heated to 250° C. for 45 minutes in a stream of inert gas such as helium, nitrogen, or argon. The flow of inert gas is continued through the material after heating has ceased until it comes to room temperature. Then it is preferably held for a day before being used. It is not sensitive to air for short periods of time, but should be kept away from moisture.

The Porapak Q is conditioned in a similar manner by heating at 250° C. for two hours in a stream of inert gas whose flow is continued after heating ceases until the material cools to room temperature.

The valve 20 is set to direct the flow of gases through parallel columns 31A and 31B. The material in column 31B does not retain oxygen and nitrogen, which passes through unaffected within about three seconds. Carbon dioxide is retained temporarily (i.e., it is adsorbed reversibly) in column 31B and is eluted within 15 seconds. Meanwhile the material in column 31A retains $CO_2$ irreversibly, and oxygen and nitrogen are adsorbed reversibly. Oxygen is eluted first, followed by nitrogen, the oxygen coming through within about 25 seconds and nitrogen within about 30 seconds.

Figure 4:
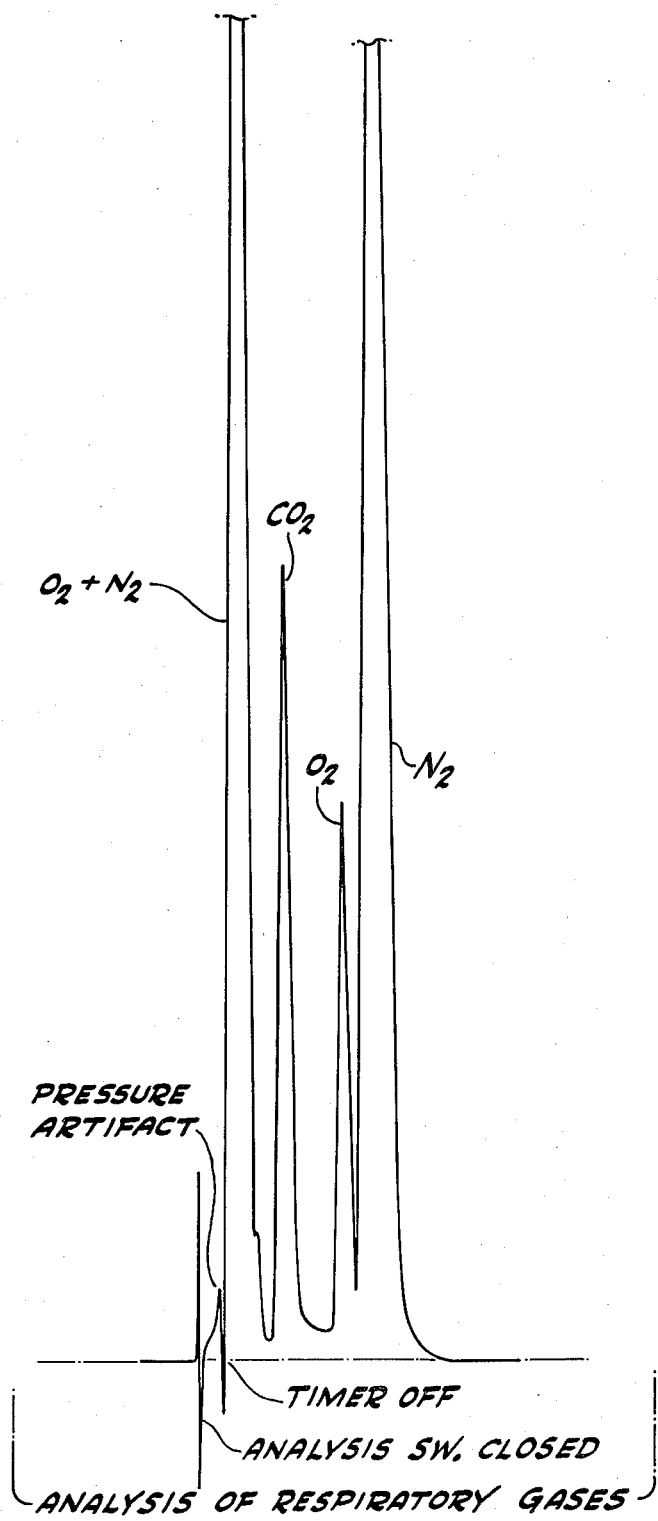
FIG. 4 is a typical tracing of the readout of an analysis of respiratory gases with the apparatus of FIG. 1.

In start-up before analysis switch 63 is closed, the carrier gas (helium) is caused to flow through the circuit including the shunt line 16 to bring the detector into a state of equilibrium with a nil output which is manifested by the trace being horizontal and along the base line. Meanwhile a sample of respiratory gas is introduced through line 40 and valve 43 into sampler 46. Then the analysis switch 63 is closed which automatically starts the timer 60. The helium then propels the sample of respiratory gas from sampler 46 through columns 31A and 31B. There results a first big peak indicating oxygen and nitrogen, then a carbon dioxide peak 10 to 15 seconds after closing analysis switch 63, then an oxygen peak in about 20 to 25 seconds, and then a nitrogen peak in about 25 to 30 seconds. These peaks are labeled in FIG. 4 which also shows the closing of switch 63, the start of timer 60, the stopping of timer 60 and a peak which is a pressure artifact. The pressure artifact, $O_2+N_2$ and the $N_2$ peaks are not of significance and the $O_2+N_2$ and $N_2$ peaks are off scale.

EXAMPLE 2. DETERMINATION OF PULMONARY FUNCTION

For this purpose valve 20 is set to route gas through column 25 which is filled with 13X treated as described above. It is first necessary to determine the dilution factor, that is to say, the volume of gas in the lungs after exhalation. This column is $48''\pm 2''$ long and $\frac{1}{4}''$ in diameter. The patient inhales a mixture of gas as follows:

Ne=0.3-0.5%

CO=0.3-0.5%

Room air=balance

This gas is dry.

Figure 5:
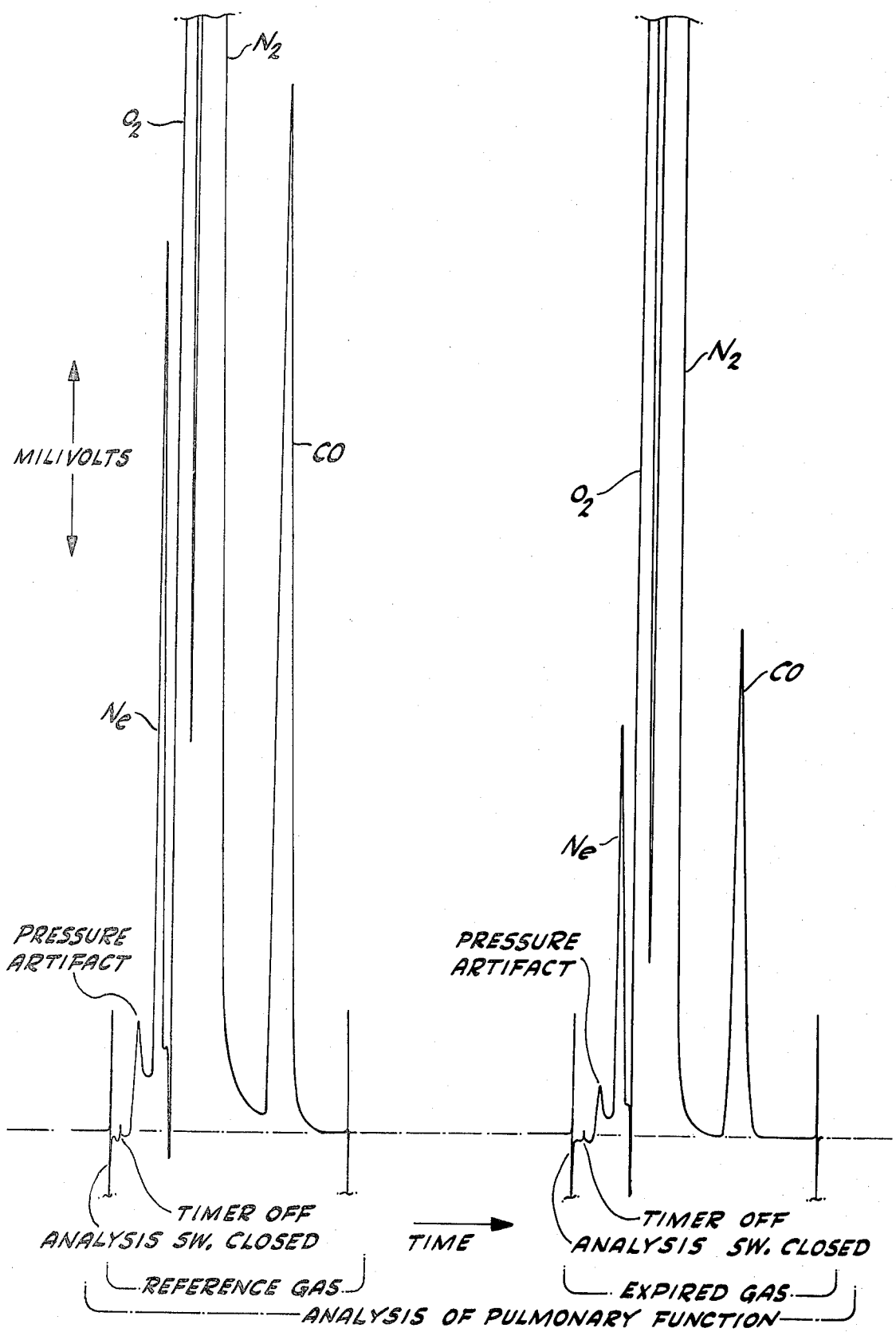
FIG. 5 is a typical tracing of the readout of an analysis indicating pulmonary function resulting from use of the apparatus of FIG. 1.

The patient exhales fully, then inhales this gas, being instructed to inhale to the fullest possible extent. Then the patient is instructed to exhale as fast and as fully as possible after holding his breath for 10 seconds. The exhaled gas is collected in a balloon and introduced into sampler 46 or is exhaled directly into a mouthpiece connected to line 40 shown in FIG. 1. Then the analysis switch 63 is closed, valve 20 having been set to direct flow of gas through column 25. This column holds $CO_2$ irreversibly and it adsorbs neon, oxygen, nitrogen and CO and releases them in that order. In about 10 to 15 seconds the adsorbed neon is eluted and appears, producing a corresponding peak; then oxygen, after about 40 seconds, appears; and then nitrogen after about 50 seconds; and CO after 60 to 70 seconds. This gives rise to Ne, $O_2+N_2$ and CO peaks as shown in FIG. 5. (The $O_2$ and $N_2$ peaks overlap and are off scale but that is not significant.) The ratio $$\frac{Ne_{expired}}{Ne_{inspired}}$$

is the dilution factor. From this dilution factor the total lung volume is determined by the following equation.

$$\text{Total lung volume} = \frac{\text{Volume of gas inspired}}{\text{Dilution factor}}$$

From the total lung volume, so calculated, the lung diffusing capacity (DLC) is determined by the following equation:

$$\frac{TLV \times 60}{(BP - 47) \times (BHT)} \times \ln \frac{(Ne)_e/(Ne)_i}{(CO)_e/(CO)_i}$$

TLV = total lung volume

BP = barometric pressure

BHT = breath holding time $(Ne)_e$ = neon expired (FIG. 5—right)

$(Ne)_i$ = neon inspired (FIG. 5—left)

$(CO)_e$ = CO expired (FIG. 5—right)

$(CO)_i$ = CO inspired (FIG. 5—left)

In the description above certain dimensions and other factors and parameters and certain materials (gaseous and solid) are referred to. It will be understood that other dimensions, factors, parameters and materials may be used. Thus the adsorbent materials for the column or columns will be selected in accordance with the components of the gas to be analyzed and the purpose of the analysis to selectively pass (without adsorption) and to adsorb different components of the gas; e.g., to pass without adsorption a carrier gas and in some cases a component of the gas to be analyzed which is of no interest; to adsorb reversibly a single component of a gas where that is the only component to be measured and to allow elution of such component by carrier gas after the lapse of a short interval of time; and/or to adsorb reversibly two or more components of interest and to allow their elution by carrier gas within a short interval of time of the order of 60 seconds but in time sequence such that each such component is completely eluted and peaks before the next component commences its elution. Other adsorbents than Porapak Q and 13X may be employed, e.g., hexamethyl phosphoramide (HMPA), silica gel, molecular sieve 5A (a diatomaceous earth), Porapak T and N (polystyrenes), etc. Other molecular species of gas that may be analyzed include acetylene (to measure pulmonary blood circulation), anesthetic gases such as cyclopropane; methane, sulfur hexafluoride, etc. Carrier gases other than helium include argon, nitrogen (alone or in admixture with helium), room air (dry, usually in admixture with other gases), etc.

Among the advantages of the apparatus and method of the invention are the following:

By reason of the small (3 milliliter) sample of gas and the re-routing of the carrier gas shortly (about 5 seconds) after the analysis switch 63 is closed, a mixing effect, which would result from continued passage of carrier gas through the sampler 46, is avoided. By use of a very small (3 milliliter) sample of gas, sharper peaks result than with larger samples such as 5–8 milliliters (requiring other apparatus). The detector circuit is very sensitive. The thermistors 50A and 50B do not require heating; they are enclosed in a relatively massive block and are therefore at ambient temperature plus the temperature to which they are heated by passage of a small (e.g., 6 milliamp) current through them. The temperature difference between them is a function of the composition and velocity of the gas passing over the ceramic semiconductors. The velocity remains constant, therefore the only variable is gas composition. The small size of these semiconductors enables them to respond quickly to small changes in gas composition.

The employment of parallel columns 31A and 31B and the proportioning of and simultaneous flow of gas through both columns and into the detector 10 is advantageous because it allows a complete analysis of $CO_2$ and $O_2$ within 30 seconds and without the need to switch from one column to the other. Switching (which is required by one well known thermistor type chromatograph presently on the market) is disadvantageous for several reasons. One reason is that an operator must observe the recording and determine when to switch from one column to another and must do so quickly or he will lose the sample. Another reason is that when switching is done the apparatus must also be readjusted to locate the base line properly and the attenuator must also be adjusted. In the arrangement shown and described above, the peaks of interest ($CO_2$ and $O_2$) are sharply separated, no switching is required and the base line remains the same throughout the analyses, and no changes in attenuator setting are required going from $CO_2$ (3–5%) to oxygen (15–20%).

In both the parallel column (such as 31A, 31B) and single column (such as 25) embodiments of the invention, the gaseous components of interest are adsorbed and then eluted in a time ordered sequence such that each component of interest exhibits a sharp peak rising steeply from and descending steeply to a single base line. In part this is due to the employment of a very small (such as 3 ml) sample of gas and in part it is due to the automatic (time related) switching of the flow of carrier gas from the sampler path to the shunt (line 16) path. This is accomplished by switching to the shunt path 16 as soon as possible after the bolus or sample of gas passes through valve 17. Premature switching would result in mixing the bolus with the carrier gas. Overly delayed switching will result in inaccuracies.

I claim:

1. In a chromatograph apparatus of the type comprising:
   (1) At least one body of adsorptive material, each such body having an inlet and an outlet, and each having the properties of adsorbing one or more components of a gaseous mixture to be analyzed, of allowing one or more of the adsorbed components to be eluted by passage of an inert carrier gas through the body and, where two or more gaseous components are to be adsorbed by and eluted from a single body, of causing elution of such components in time ordered sequence such that the eluted components are not commingled in the gas leaving the outlet of such body,
   (2) a detector having a test conductor, a reference conductor, an electrical circuit including said conductors, said circuit having a nil output when said conductors are at the same temperature and having an output when the conductors are at different temperatures which is proportional to the difference in temperatures, said conductors being sensitive to the thermal conductivity of a gas in contact therewith, said detector having a first gas inlet and a first gas outlet for conducting carrier gas into, through and out of the detector in thermal contact with the reference conductor; said detector also having a second inlet and a second outlet for conducting gas into, through and out of the detector in thermal contact with the test conductor, the improvement which comprises:
   (a) a first gas circuit connecting the first detector outlet with the second detector inlet, said circuit including as a portion thereof said body or bodies of adsorptive material by way of the inlet and outlet of each,
   (b) a second gas circuit having an inlet end and an outlet end and which is parallel to a portion of said first gas circuit, said second circuit being connected as its inlet end to the first circuit by a first valve means and being connected at its outlet end to the first circuit by a second valve means, said second gas circuit including a sampler element for receiving a predetermined volume of gas to be analyzed, said second gas circuit being located upstream in relation to said body or bodies,
   (c) valve operating means for said valve means operable automatically to carry out the following cycle of operation:
      (i) acting initially to route carrier gas solely through the first gas circuit from the first detector outlet to the second detector inlet,
      (ii) then acting upon commencement of analysis to route carrier gas from the first detector outlet through said first valve means to said second gas circuit to propel said sample of gas from the sampler though said second valve means, thence through the remainder of said first gas circuit including said body or bodies of adsorptive material to the second detector inlet, and
      (iii) after said sample of gas has been propelled beyond said second valve means, acting to re-establish flow of carrier gas solely through said first circuit.

2. The apparatus of claim 1 wherein there are at least two bodies of adsorptive material having their inlets and outlets in parallel, the composition and geometry of said parallel bodies being selected to absorp gaseous components $G_1$, $G_2-G_n$ wherein n is a positive integer, and to cause elution of those of $G_1-G_n$ which are to be determined in time ordered sequence whereby the concentration of each such component as delivered to the second inlet of the detector peaks separately and distinctly from all other peaks, the flow of gas through said parallel bodies being simultaneous.

3. The apparatus of claim 1 wherein said conductors are thermistors.

4. A chromatograph for determining pulmonary function comprising:
   (a) a detector coupled to a recorder for recording the output of the detector,
   (c) said detector comprising a circuit including a reference thermistor and a test thermistor both of which are heated by passage of electric current and are sensitive to the thermal conductivity of a gas in contact therewith, such thermistors when exposed at ambient temperature to a gas of the same composition result in a null output of the detector and when the test thermistor is exposed to a test gas of different composition than the reference thermistor result in an output of the detector which is characteristic of the composition of the test gas,
   (c) said detector having a first gas inlet and a first gas outlet for exposing the reference thermistor to thermal contact with a flow of inert carrier gas and a second gas inlet and a second gas outlet for exposing the test thermistor to thermal contact with a flow of gas,
   (d) parallel first and second gas circuits, said first gas circuit having an inlet end connected to the first detector outlet and an outlet end connected to the second detector inlet and including as part of such circuit a column of adsorptive material capable of adsorbing neon and carbon monoxide or acetylene and of allowing elution of such gases by an inert carrier gas within a time period not greatly in excess of 75 seconds, one of such species being eluted first and the other being eluted later within such time period and producing two distinct, separate peaks on the recorder,
   (e) such second gas circuit being connected at its inlet end to said first circuit downstream from the first detector outlet by a first valve and being connected by a second valve at its outlet end to said first gas circuit downstream from said first valve and upstream from said column, said second gas circuit including a sampler element for holding a predetermined small quantity of gas to be analyzed, and
   (f) valve operating means operable to carry out the following cycle of operations:
      (i) first routing inert carrier gas solely through the first gas circuit from the inlet end to the outlet end thereof,
      (ii) then upon commencement of analysis routing said carrier gas from said first detector outlet through said first valve means and by way of said second gas circuit to propel said sample of gas through said second valve and the remainder of said first gas circuit including said column, and
      (iii) after the sample of gas has been propelled beyond said second valve, restoring the initial flow of carrier gas solely through said first circuit, such restoration occurring after a time interval sufficiently short to ensure the production of sharp neon and CO or acetylene peaks on the recorder.

5. A method of gas analysis by selective adsorption of one or more components of a gaseous mixture by a body of adsorptive material, elution of one or more of the adsorbed components and flow of the eluted gas in thermal contact with an element of an electrical detector whose output is a function of the temperature of such element, said method comprising the following steps:
 (a) first causing flow of a carrier gas in thermal contact with said element,
 (b) then interrupting such flow of carrier gas and propelling a sample of gaseous mixture to be analyzed through said body of adsorptive material and then in thermal contact with said element, said material and its geometry being selected to adsorb one or more components of the sample, to allow elution of one or more of the adsorbed components by a stream of carrier gas and, where two or more components are to be adsorbed, eluted or determined, allowing elution of each such component separately and without overlap with any other eluted component of the gaseous mixture,
 (c) then restoring flow of carrier gas through said body of adsorptive material of effect elution,
 (d) step (c) being carried out after a very short interval of time following step (b) to allow the sample at least to reach the adsorptive material without being mixed with carrier gas, such interval being short enough to minimize inaccuracies resulting from delayed restoration of flow of carrier gas.

6. The method of claim 5 wherein step (b) is accomplished by diverting flow of carrier gas.

* * * * *